US010206823B2

(12) United States Patent
Sheehan et al.

(10) Patent No.: US 10,206,823 B2
(45) Date of Patent: Feb. 19, 2019

(54) DISPOSABLE DIAPER WITH CONVENIENT LAY-OPEN FEATURES

(71) Applicant: The Procter & Gamble Company, Cincinnati, OH (US)

(72) Inventors: Astrid Annette Sheehan, Symmes Township, OH (US); Nelson Edward Greening, II, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 484 days.

(21) Appl. No.: 14/875,729

(22) Filed: Oct. 6, 2015

(65) Prior Publication Data

US 2017/0095378 A1    Apr. 6, 2017

(51) Int. Cl.
| A61F 13/15 | (2006.01) |
| A61F 13/49 | (2006.01) |
| A61F 13/62 | (2006.01) |
| A61F 13/56 | (2006.01) |
| A61F 13/53 | (2006.01) |

(52) U.S. Cl.
CPC .. *A61F 13/49014* (2013.01); *A61F 13/49011* (2013.01); *A61F 13/49019* (2013.01); *A61F 13/5633* (2013.01); *A61F 13/62* (2013.01); *A61F 2013/49092* (2013.01); *A61F 2013/530343* (2013.01)

(58) Field of Classification Search
CPC .......... A61F 13/49014; A61F 13/49011; A61F 13/49019; A61F 13/5633; A61F 13/62
USPC .................... 604/391, 387, 389, 386, 385.24
See application file for complete search history.

(56) References Cited

U.S. PATENT DOCUMENTS

| 3,860,003 A | 1/1975 | Buell |
| 3,929,135 A | 12/1975 | Thompson |
| 4,151,240 A | 4/1979 | Lucas et al. |
| 4,324,246 A | 4/1982 | Mullane et al. |
| 4,342,314 A | 8/1982 | Radel et al. |
| 4,463,045 A | 7/1984 | Ahr et al. |
| 4,472,328 A | 9/1984 | Sugimoto et al. |
| 4,552,709 A | 11/1985 | Koger, II et al. |
| 4,591,523 A | 5/1986 | Thompson |
| 4,610,678 A | 9/1986 | Weisman et al. |
| 4,673,402 A | 6/1987 | Weisman et al. |
| 4,834,735 A | 5/1989 | Alemany et al. |
| 4,888,231 A | 12/1989 | Algstadt |
| 4,892,536 A | 1/1990 | Des Marais et al. |
| 4,990,147 A | 2/1991 | Freeland |

(Continued)

FOREIGN PATENT DOCUMENTS

WO    WO 95/16746 A1    6/1995

OTHER PUBLICATIONS

PCT International Search Report, dated Jan. 3, 2017 (10 pages).
U.S. Appl. No. 14/875,279, filed Oct. 6, 2015, Sheehan et al.
13909 Office Actions for U.S. Appl. No. 15/197,961.

*Primary Examiner* — Jacqueline Stephens
(74) *Attorney, Agent, or Firm* — Daniel S. Albrecht

(57) ABSTRACT

A disposable diaper having features that improve its ability to lay open in a flat configuration is disclosed. The diaper may include fastening members having a minimum basis weight, and a minimum width and a minimum surface area relative the chassis dimensions, along with other features that tend to cause the diaper to lay open in a flat configuration, for the convenience of the caregiver during application of the diaper to a baby.

20 Claims, 12 Drawing Sheets

(56) References Cited

U.S. PATENT DOCUMENTS

| | | |
|---|---|---|
| 5,037,416 A | 8/1991 | Allen et al. |
| 5,137,537 A | 8/1992 | Herron et al. |
| 5,147,345 A | 9/1992 | Young et al. |
| 5,151,092 A | 9/1992 | Buell et al. |
| 5,221,274 A | 6/1993 | Buell et al. |
| 5,260,345 A | 11/1993 | DesMarais et al. |
| 5,265,222 A | 11/1993 | Nishiya et al. |
| 5,266,392 A | 11/1993 | Land et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | LaVon et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,685,874 A | 11/1997 | Buell et al. |
| 5,733,628 A | 3/1998 | Pelkie |
| 5,865,823 A | 2/1999 | Curro |
| 5,916,661 A | 6/1999 | Benson et al. |
| 6,004,306 A | 12/1999 | Robles et al. |
| 6,107,537 A | 8/2000 | Elder et al. |
| 6,169,151 B1 | 1/2001 | Waymouth et al. |
| 6,410,129 B2 | 6/2002 | Zhang et al. |
| 6,518,378 B2 | 2/2003 | Waymouth et al. |
| 6,555,643 B1 | 4/2003 | Rieger |
| 6,559,262 B1 | 5/2003 | Waymouth et al. |
| 6,632,385 B2 | 10/2003 | Kauschke et al. |
| 6,645,569 B2 | 11/2003 | Cramer et al. |
| 6,794,024 B1 | 9/2004 | Walton et al. |
| 6,863,933 B2 | 3/2005 | Cramer et al. |
| 7,112,621 B2 | 9/2006 | Rohrbaugh et al. |
| 7,307,031 B2 | 12/2007 | Carroll et al. |
| 7,507,587 B2 | 3/2009 | Chiba et al. |
| 8,177,766 B2 | 5/2012 | Mansfield |
| 8,529,725 B2 | 9/2013 | Bishop et al. |
| 8,728,051 B2 | 5/2014 | Lu et al. |
| 8,939,957 B2 | 1/2015 | Raycheck et al. |
| 8,979,815 B2 | 3/2015 | Roe et al. |
| 8,992,499 B2 | 3/2015 | Kline et al. |
| 9,068,912 B2 | 6/2015 | Kline et al. |
| 9,326,899 B2 | 5/2016 | Zink et al. |
| 9,532,908 B2 | 1/2017 | Wade et al. |
| 9,532,910 B2 | 1/2017 | Rosati et al. |
| 2003/0148684 A1 | 8/2003 | Cramer et al. |
| 2004/0092677 A1 | 5/2004 | Hanke et al. |
| 2006/0057921 A1 | 3/2006 | Turi |
| 2006/0173436 A1 | 8/2006 | Krautkramer et al. |
| 2007/0073256 A1 | 3/2007 | Ponomarenko et al. |
| 2007/0142815 A1* | 6/2007 | Macura ............... A61F 13/58 604/389 |
| 2011/0092943 A1 | 4/2011 | Bishop et al. |
| 2012/0316526 A1 | 12/2012 | Rosati et al. |
| 2012/0316528 A1 | 12/2012 | Kreuzer et al. |
| 2014/0134910 A1 | 5/2014 | Mansfield |
| 2014/0163506 A1 | 6/2014 | Roe et al. |
| 2014/0163511 A1 | 6/2014 | Roe et al. |
| 2014/0200543 A1 | 7/2014 | Chatterjee et al. |
| 2015/0080837 A1 | 3/2015 | Rosati et al. |
| 2015/0088088 A1 | 3/2015 | Wade et al. |
| 2016/0022510 A1 | 1/2016 | Hashimoto et al. |

* cited by examiner

DISPOSABLE DIAPER WITH CONVENIENT LAY-OPEN FEATURES

BACKGROUND OF THE INVENTION

In recent years, advancements in the designs of disposable diapers and component materials, including the use of substantially cellulose-free absorbent cores, and improvements to strength and appearance and feel of nonwoven and film materials, have resulted in substantial reductions in weight and bulk of the components of many varieties of diapers currently sold.

Weight and bulk reduction, while having advantages, may also present disadvantages.

Several factors may contribute to creation of a diaper that does not reliably lay conveniently flat on a changing table after being withdrawn from its package and opened from its packaged, folded configuration by the caregiver. The materials of the diaper may take on a "set" in the package, which may cause the diaper to tend to return to the folded configuration. Included longitudinal elastic components may pull thin and light components of the diaper longitudinally on the wearer-facing side, tending to draw its waist edges toward each other. Reduced bulk (i.e., reduced thickness) may result in loss of stiffness in the diaper that would otherwise tend to cause it to resist bending. If the diaper does not have sufficient weight and/or weight distribution among its various components sufficient to enable it, after being opened, to resist the forces tending to cause it to return toward the folded/packaged configuration, it may tend to do so.

Thus, if not continuously held open on the table by a hand, the baby's body or other object placed over it, the diaper may tend not to reliably lay flat on the changing table in the most convenient position for application to the baby. This can necessitate extra effort from the caregiver during a diaper change, and frustration, particularly when the caregiver is attempting to apply the diaper to an active or uncooperative baby.

Thus, there is room for improvements in the design of disposable diapers that makes them more convenient while retaining the advantages of other most recent design developments.

DETAILED DESCRIPTION OF EXAMPLES

Definitions

Figure 1:
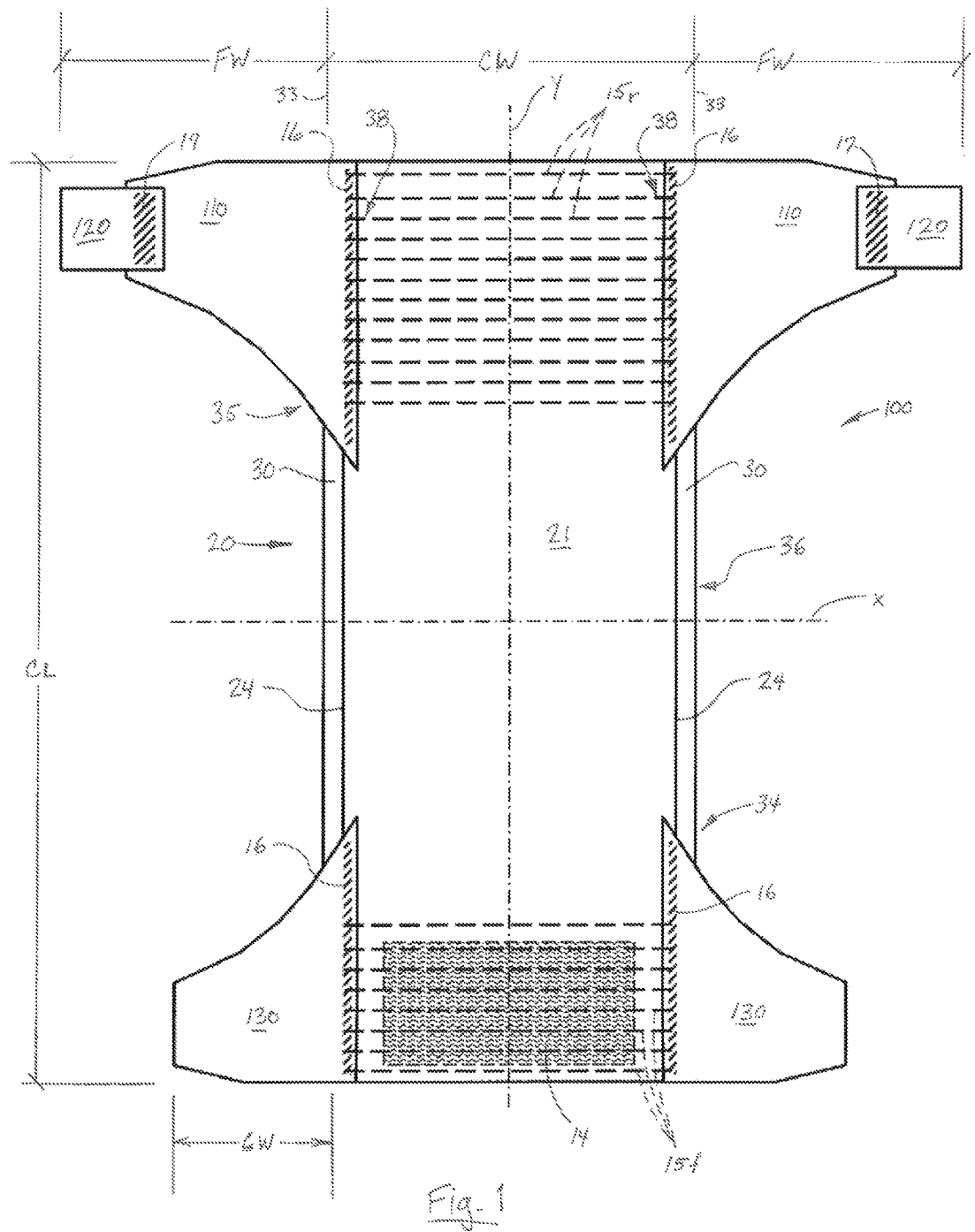
FIG. 1 is a schematic plan view of an example of a tape diaper laid out flat and in an extended condition, open and extended to the full dimensions of its web components with elastic-induced contraction pulled out, with garment-facing surfaces facing the viewer.

"Continuous," with respect to a mechanical bond joining two or more web materials along a bond line, means that there is no line perpendicular to the bond line that does not cross a bonded area. As such, a "continuous" bond may be formed by a plurality of discrete bond areas disposed along the bond line, as is illustrated by way of non-limiting example in FIG. 1 (mechanical bond 16).

As used herein, the term "elastic" or "elastomeric" refers to the property of an extensible material (or a composite of multiple materials) that can extend, without substantial rupture or breakage, to a strain of 100% in the Hysteresis Test, with a set less than or equal to 10% of the elongation as measured according to the Hysteresis Test. An elastic material is considered elastically extensible.

"Extended condition," with respect to a tape diaper that includes pre-strained elastic members, means extended out laterally and longitudinally to the full dimensions of the web components of the chassis, against any contraction induced by the pre-strained elastic members, and with any gathers in the web components pulled out and flattened.

"Film" means a non-fibrous skin- or membrane-like material formed in part or in whole of one or more polymer resins.

"Integrally-formed," for purposes herein and with respect to a fastening member having a fastener attached thereto, means a fastening member that has one or both of the following characteristics: (1) It has no inboard- and longitudinally inward-pointing vertex lying along its first or second outermost lateral edges, and lying between the inboard edge of the fastener zone and a junction line; and/or (2) there is at least one longitudinal line along the end region, along which a layer of material forming the end region is longitudinally coextensive with, or longer than, a layer of material forming an extensible zone. These characteristics structurally and functionally distinguish a fastening member having one or both of them from a fastening member having a "tape" type construction, in which a comparatively short tab member, bearing a fastener and forming the end region of the fastening member, joins a relatively longer side panel region of the fastening member, in which such vertices are present and no such line exists.

"Lateral" and forms thereof refer to the direction parallel to the waist edges of a tape diaper, and perpendicular to the longitudinal direction, such as indicated by the direction of lateral axis x depicted in the figures. "Width" refers to a dimension measured in the lateral direction.

"Longitudinal" and forms thereof refer to the direction perpendicular to the waist edges of a tape diaper, and perpendicular to the lateral direction, such as indicated by the direction of longitudinal axis y depicted in the figures. "Length" refers to a dimension measured in the longitudinal direction.

"Laterally outboard" with respect to the longitudinal axis of a diaper means in a direction laterally away from the longitudinal axis. "Longitudinally outboard" with respect to the lateral axis of a diaper means in a direction longitudinally away from the lateral axis. "Laterally inboard" with respect to the longitudinal axis means in a direction laterally toward the longitudinal axis. "Longitudinally inboard" with respect to the lateral axis means in a direction longitudinally toward the lateral axis.

A "mechanical bond" is a bond between two or more materials in which the respective materials have been deformed and physically intermixed, intertwined or intermingled at one or more bonded areas, and includes but is not limited thermal bonds and compression bonds.

"Nonwoven," or interchangeably, "nonwoven web" means a fibrous cloth-like material formed of discrete staple fibers, or long or substantially continuous fibers or filaments, or any combination thereof, the fibers and/or filaments being neither knitted nor woven, but rather, distributed along a plane in at least somewhat random orientation, accumulated, consolidated and held together to form a cohesive web structure by one or more of friction, entanglement, adhesive bonding, through-air (melt) bonding, thermal bonding or other bonding. Nonwovens may be formed by processes including, for example, spunbonding, meltblowing, airlaying, coforming and carding, hydroentangling and/or other processes used to manufacture such materials.

The "outer leg elastic lines" are the two longitudinal lines along a diaper that are the laterally outboard-most tangents to the two laterally outboard-most leg cuff elastic members on the respective left and right sides of the diaper, when the diaper is in an extended condition. Examples are illustrated as lines 33 in FIGS. 1 and 2, as the longitudinal lines tangent to the laterally outboard-most leg cuff elastic members 31.

"Pre-strained," with respect to an elastic member in a tape diaper, means that the elastic member has been incorporated into the diaper structure while in a strained condition, such that upon completion of manufacturing and relaxation of the diaper structure, the elastic member contracts toward its unstrained dimension(s) and causes the material surrounding it to form gathers of such material generally transverse to the direction of strain.

Figure 2:
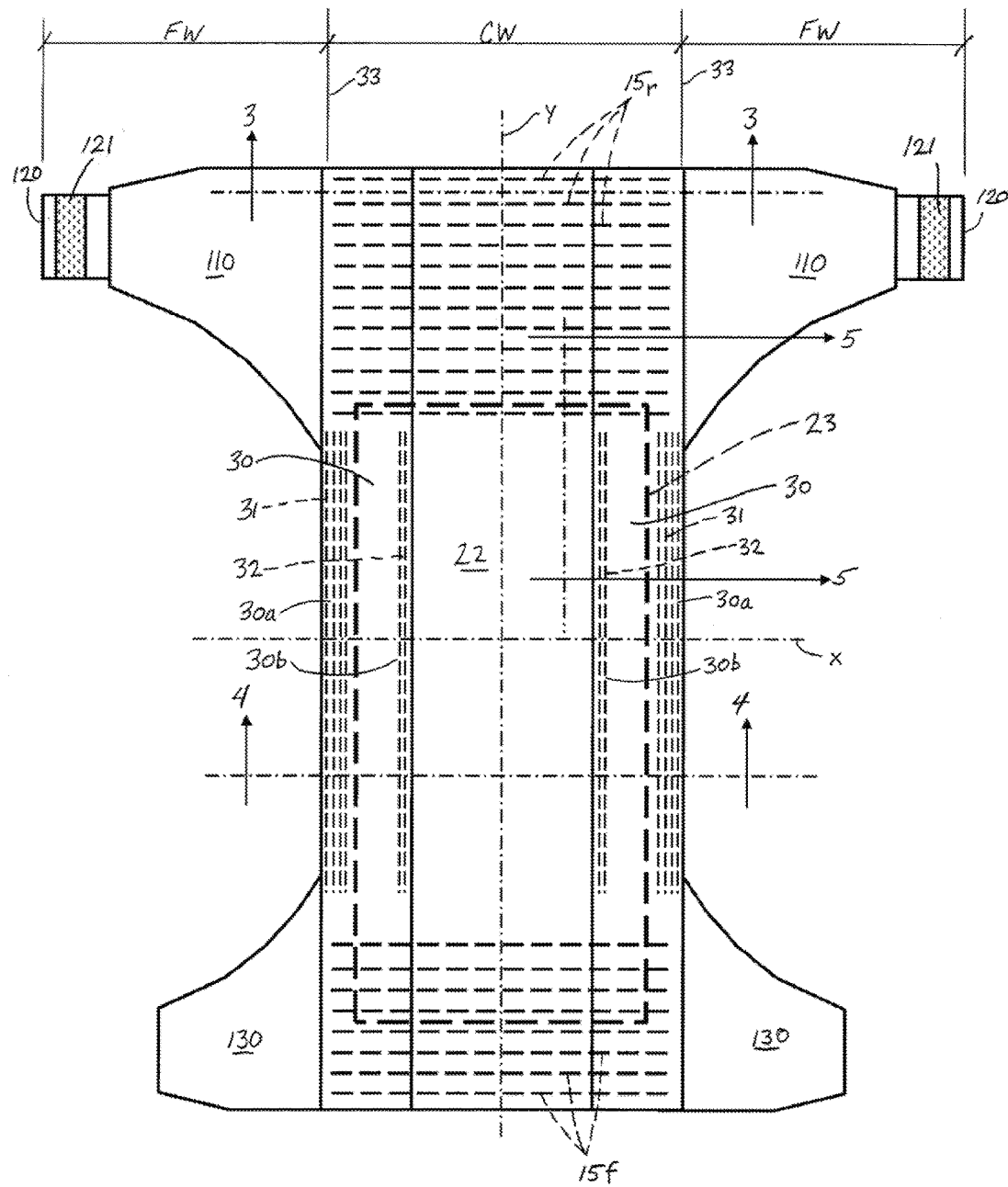
FIG. 2 is a schematic plan view of the diaper of FIG. 1, laid out flat, open and extended to the full dimensions of its web components with elastic-induced contraction pulled out, with wearer-facing surfaces facing the viewer.

Currently, disposable diapers generally are manufactured in two configurations: The "tape" configuration and the "pant" configuration. Pant configuration diapers are typically packaged with front and rear side or hip panels fastened or seamed together such that the product resembles a pair of briefs or underwear. These are typically marketed for wear by toilet-training toddlers or by older children experiencing childhood enuresis. Tape configuration diapers are typically marketed for use with younger babies, and are typically packaged in a folded but an unfastened configuration, such that a diaper may be withdrawn from the package, opened toward a flat configuration such as depicted in FIG. 2, ready to be pushed rear-waist-edge-first to a location beneath a reclining baby's buttocks/lower torso or to have the baby lowered thereonto in a reclining position, for fitting and fastening. In the past, many tape diapers literally had sections or tabs of material bearing adhesive, disposed at the ends of fastening members; the adhesive tab was pulled around the baby's hips and adhered to the front waist region of the diaper. More recently some diapers have substituted hook-and-loop fastening systems for adhesive, and some diapers have eliminated the tabs altogether, disposing hooks patches directly on the fastening members. The term "tape diaper" used herein is only intended to distinguish the product from pant diapers. The term is not to be limited to mean a diaper with adhesive tabs or other tabs; it applies to any diaper having fastening members with distal ends that are not permanently attached to another portion of the diaper.

From observations of caregivers applying tape diapers to babies, it has been learned that a tape diaper that does not tend to reliably remain in an open position after being opened and laid down on a flat horizontal surface, i.e., a diaper having one or more components that tend to bunch, fold, crumple or return to the folded configuration, create the need for extra effort by the caregiver to apply to a baby. The caregiver is required to expend extra time and effort to open and arrange the diaper a second time and/or hold it in the open configuration to make it ready for application to the baby. Observations have shown that this can be source of frustration for the caregiver and dissatisfaction with the diaper product, particular when the baby is uncooperative during the diaper change.

Figure 3A:
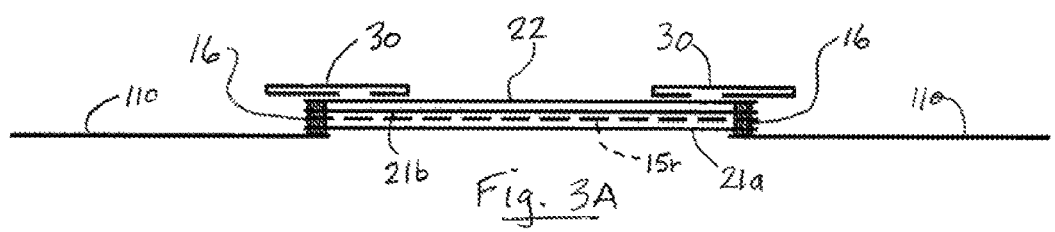
FIG. 3A is a schematic lateral partial cross-section of the diaper of FIG. 2, taken along line 3-3 shown in FIG. 2.
Figure 3B:
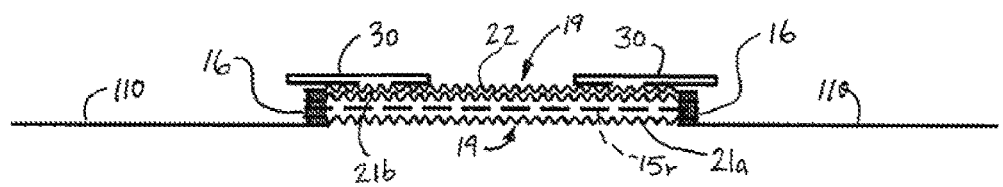
FIG. 3B is a schematic lateral partial cross-section of the diaper of FIG. 2, take along line 3-3 shown in FIG. 2, and shown with the diaper in a laterally relaxed condition in which gathers form in some of the components.
Figure 4:
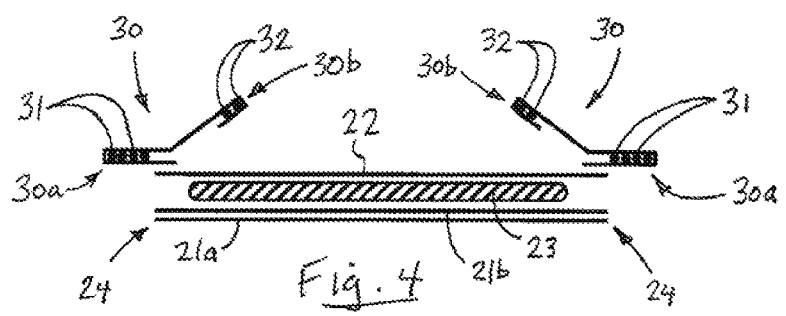
FIG. 4 is a schematic lateral cross-section of the diaper of FIG. 2, taken along line 4-4 shown in FIG. 2.
Figure 5:
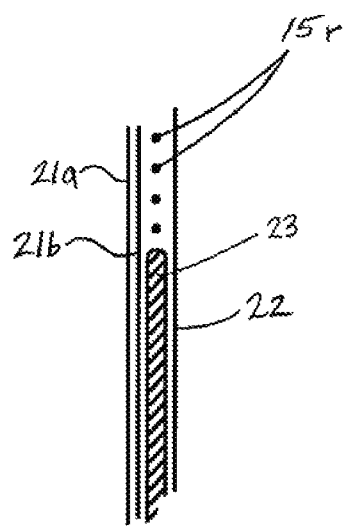
FIG. 5 is a schematic longitudinal partial cross-section of the diaper of FIG. 2, taken along line 5-5 shown in FIG. 2.

FIGS. 1 and 2 schematically depict a plan views of a disposable diaper 100 laid out in opened and extended condition. FIGS. 3A, 3B and 4 schematically depict cross section views of the diaper, taken at lines 3-3 and 4-4 shown in FIG. 2.

Diaper 100 may include a central chassis 20, having front waist region 34, rear waist region 35, and crotch region 36. Lateral axis x and longitudinal axis y of the central chassis, equally dividing front and rear portions and left and right portions, respectively, are identified in the figures for reference. Chassis 20 may include topsheet 22, backsheet 21, and absorbent core structure 23 disposed between the topsheet and backsheet. Backsheet 21 may be formed of a single liquid impervious layer, or may be formed of a laminate of two or more layers such as outer cover 21a, and liquid barrier 21b, in which liquid barrier 21b renders the backsheet liquid impervious. Diaper 100 may include fastening members 110 extending laterally from each side of the chassis, in either the front 34 or rear waist region 35, although, generally, disposing the fastening members in the rear waist region may be more desirable due to the manner in which tape diapers are typically applied to reclining babies by caregivers. Fastening members 110 may further include fastening tabs 120 disposed proximate the distal ends thereof. Fastening tabs 120 may have disposed thereon a fastener 121 such as, but not limited to, a strip or patch of applied adhesive, or a strip or patch of hooks material forming part of a hook-and-loop fastening system. Fastening tabs 120 may be bonded to fastening members 110 by suitable bonds 17, which may be mechanical bonds, adhesive bonds or a combination thereof.

In one alternative example, however, a fastener 121 such as a strip or patch adhesive or hooks material may be disposed directly on a suitably configured main portion of fastening member 110, such as an integrally formed fastening member as described in U.S. Pat. No. 9,068,912, and the tab 120 may be omitted. The garment facing surface of front waist region 34 may have a landing zone 14 disposed thereon, which may comprise a suitable receiving surface for adhesive on a fastening member, or a patch of suitable loops material affixed to the garment-facing surface of the backsheet, for receiving and anchoring hooks on a fastening member. In one alternative, however, landing zone 14 may be provided by and be integral with an outer cover 21a nonwoven material with fiber components suitably adapted and bonded so as to effectively receive and anchor hooks on a fastening member, eliminating the need for a separate patch of loops material. Chassis 20 also may have grasping members 130 extending laterally from the waist region not occupied by fastening members 110. Chassis 20 may include cuff structures 30, which may include leg cuff elastic members 31 selected, pre-strained and disposed so as to tend to draw leg cuffs 30a snugly about the wearer's legs, and barrier cuff elastic members 32, selected, pre-strained and disposed to as to tend to pull barrier cuffs 30b to stand upright such that they snugly rest against the baby's skin through the crotch area on either side, thereby forming a containing structure to contain exudates within the diaper structure.

Topsheet

The chassis 20 may include a liquid permeable topsheet 22, a backsheet 21, and an absorbent core structure 23 between the topsheet 22 and the backsheet 21. The absorbent core structure 23 may have a body-facing surface and a garment facing-surface. The topsheet 22 may be joined to the core structure 23 and/or the backsheet 21. The backsheet 21 may be joined to the core structure 23 and/or the topsheet 22. It should be recognized that other structures, elements, or substrates may be positioned between the core structure 23 and the topsheet 22 and/or backsheet 21. While the topsheet 22, the backsheet 21, and the absorbent core structure 23 may be assembled in a variety of configurations, examples are described generally in U.S. Pat. Nos. 3,860,003; 5,151,092; 5,221,274; 5,554,145; 5,569,234; 5,580,411; and 6,004,306.

The topsheet 22 is generally a portion of the chassis 20 that may be positioned at least in partial contact or close proximity to a wearer. Suitable topsheets 22 may be manufactured from a wide range of materials, such as porous foams; reticulated foams; apertured plastic films; or woven or nonwoven webs of natural fibers (e.g., wood or cotton fibers), synthetic fibers (e.g., polyester, polyolefin e.g. polyethylene or polypropylene fibers), or a combination of natural and synthetic fibers. The topsheet 22 is generally supple, soft feeling, and non-irritating to a wearer's skin. Generally, at least a portion of the topsheet 22 is liquid pervious, permitting liquid to readily penetrate through its thickness. One topsheet material useful herein is available from BBA Fiberweb, Brentwood, Tenn. as supplier code 055SLPV09U.

Any portion of the topsheet 22 may be coated with a lotion or skin care composition. Examples of suitable lotions include those described in U.S. Pat. Nos. 5,607,760; 5,609,587; 5,635,191; and 5,643,588. The topsheet 22 may be fully or partially elasticized or may be foreshortened so as to provide a void space between the topsheet 22 and the core structure 23. Exemplary structures including elasticized or foreshortened topsheets are described in more detail in U.S. Pat. Nos. 4,892,536; 4,990,147; 5,037,416; and 5,269,775.

Backsheet

The backsheet 21 is generally positioned such that it may be at least a portion of the garment-facing surface of the pant. Backsheet 21 may be designed to prevent the exudates absorbed by and contained within the pant from soiling articles that may contact the disposable diaper 100, such as bed sheets or outer clothing. In some examples, the backsheet 21 is effectively liquid-impermeable. Suitable backsheet 21 materials include films such as those manufactured by Tredegar Industries Inc. of Terre Haute, Ind. and sold under the trade names X15306, X10962, and X10964. Other suitable backsheet materials may include breathable materials that permit vapors to escape from the pant while still preventing liquid exudates from passing through the backsheet 21. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 21 including, but not limited to, surface treatments, particular film selections and processing, particular filament selections and processing, etc.

Backsheet 21 may also consist of more than one layer. The backsheet 21 may comprise an outer cover 21a and an a liquid barrier layer 21b. The outer cover may be made of a pleasantly soft-feeling nonwoven material. The liquid barrier layer 21b may be made of a substantially liquid-impermeable film. In another example the liquid barrier layer 21b may be made of a substantially liquid-impermeable nonwoven, for example, a nonwoven formed at least in part of microfibers or nanofibers having a combination of hydrophobicity and numeric density per unit surface area sufficient to make the nonwoven effectively liquid impermeable under normal use conditions. The outer cover and an liquid barrier layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, various other changes and modifications can be made without departing from the spirit and scope of the invention.

Absorbent Core Structure

The absorbent core structure 23 includes the entirety of the structure and components thereof disposed between the topsheet and the backsheet, and may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

In one example, at least a portion of the absorbent core structure 23 is substantially cellulose free and contains less than 10% by weight cellulosic fibers, less than 5% cellulosic fibers, less than 1% cellulosic fibers, no more than an immaterial quantity of cellulosic fibers or no cellulosic fibers. It should be understood that an immaterial quantity of cellulosic material does not materially affect at least one of the thinness, flexibility, and absorbency of the portion of the absorbent core structure that is substantially cellulose free. Among other benefits, it is believed that when at least a portion of the absorbent core structure is substantially cellulose free, this portion of the absorbent core structure is significantly thinner and more flexible than a similar absorbent core structure that includes more than 10% by weight of cellulosic fibers. The amount of absorbent material, such as absorbent particulate polymer material present in the absorbent core structure may vary, but in certain embodiments, is present in the absorbent core structure in an amount greater than about 80% by weight of the absorbent core structure, or greater than about 85% by weight of the absorbent core structure, or greater than about 90% by weight of the absorbent core structure, or greater than about 95% by weight of the core. Exemplary absorbent structures for use as the absorbent core structure 23 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The absorbent core structure 23 and components thereof also may be constructed to provide a system of substantially longitudinally-oriented channels as disclosed in, for example, U.S. Patent Pub. No. US 2012-0316526; US 2012-0316528; U.S. patent Ser. No. 13/675,212; U.S. Pat. Nos. 8,979,815; 9,216,118; 9,216,116; and 9,532,910. As noted in the cited applications, a system of one or more substantially longitudinally-oriented channels in the absorbent core structure provides for efficient liquid distribution across the absorbent structure, and also a relatively thinner and more flexible core structure, contributing to an overall sleek, low-bulk, underwear-like look and feel to the pant structure. The channels are grooves or valleys defined through the absorbent material of the core. They may perform at least two functions, including providing passageways along which liquid may rapidly flow to reach and contact surface area of more absorbent material along the length of the absorbent core structure, and providing hinge- or joint-like structures in the absorbent core structure along which the absorbent core structure may more easily flex, providing comfort and bulk-reducing effects.

Cuff Structures

Referring to FIG. 2, chassis 20 may generally have any structure that is suitable for disposable absorbent articles such as diapers and training pants, including any of the absorbent core structure and leg cuff/gasketing structures described and depicted in U.S. Pat. No. 8,939,957, and including barrier 30b and leg 30a cuff portions of cuff structures 30.

Fastening Members; Size, Weight and Stiffness Features

Fastening members 110 may be formed of any suitable materials known in the art as suitable for forming fastening members for tape diapers, including nonwoven web materials with or without elastic members, films, strands, strips or other elastic components. Many currently marketed diapers have elasticized fastening members formed of stretch laminate material, which may be included with a tape diaper of the present invention. Stretch laminates typically include a layer of elastomeric film, or alternatively a series of longitudinally-spaced, laterally-extending strips or strands of elastomeric material, sandwiched between two layers of nonwoven web material. Suitable examples are described, for example, in U.S. Pat. Nos. 8,992,499; 9,068,912; and Ser. No. 10/016,320.

Each fastening member 110 may have a minimum size and/or weight.

It may be desired that each fastening member have a minimum fastening member width FW of at least 60 percent, more preferably at least 65 percent, still more preferably at least 70 percent, and even more preferably at least 75 percent of the chassis width CW. Herein, fastening member width FW of a fastening member is measured as the lateral distance between the outer leg elastic line adjacent the fastening member, and the distal end of the fastening member (including any discrete, non-integral tape tab 120 that may be present) with the fastening member in a relaxed state. Chassis width CW is measured with the chassis in extended condition, and is the distance between the two outer leg elastic lines; see FIGS. 1 and 2.

In the alternative or in combination with a minimum width, it may be desired that each fastening member have a minimum surface area (on one side) within its perimeter of at least 10 percent, more preferably at least 11 percent, and still more preferably at least 12 percent of the chassis surface area. For purposes herein, the "chassis surface area" is the product of the chassis width and the chassis length (CW× CL), where chassis length CL is the length of the diaper in extended condition from the front waist edge to the rear waist edge; see, e.g., FIG. 1. For purposes herein, the perimeter of the fastening member defining its surface area is the outline of the portion of the fastening member laterally outboard of the adjacent outer leg elastic line (including in the perimeter the outline of any discrete, non-integral tab such as tab 120 projecting from the fastening member) in a relaxed, flat condition.

Alternatively, or in combination with one or more of such minimum size features, the fastening member 110 may have a minimum basis weight of at least 90 gsm, more preferably at least 100 gsm, still more preferably at least 110 gsm, and still more preferably at least 120 gsm, or alternatively or in combination with the above-described minimum size features, at least 280 percent, more preferably at least 360 percent, even more preferably at least 440 percent, and still more preferably at least 520 percent of the combined basis weight of the topsheet 22 and backsheet 21 in the waist region about the longitudinal axis y, between the fastening members 110. Herein, the basis weight of a fastening member is the weight of the portion of the fastening member laterally outboard of the outer leg elastic line (including any discrete, non-integral tab such as tab 120 affixed thereto, divided by the surface area (on one side) of such portion in a relaxed, flat condition, expressed in grams/m$^2$ (gsm).

It is believed that such minimum size and weight features or combinations thereof are typically not found in currently marketed tape diapers, generally for reasons of economy of materials usage. One or a combination of one or more of these size and weight features imparted to a fastening member will contribute to causing the fastening member to tend to stay in an open, flat configuration when the diaper is opened a laid out flat on a horizontal surface.

Alternatively, or in combination with one or more of the features described herein, the fastening member may be non-elastic. "Non-elastic" with respect to a fastening member means that a majority of the material forming the fastening member within its perimeter (as described above) is not elastic in the lateral direction. For elastic and non-elastic web materials of similar basis weights that include one or more nonwoven layers, elastic web materials (such as stretch laminates) typically used to form fastening members tend to have less stiffness and tend to bend or flex more easily, as a result of the weight proportion of the relatively soft and flexible elastomeric materials and/or either pre-straining or incremental stretching that imparts longitudinal flexibility to the laminate. Stiffer materials may be more desirable as they are less apt to bend, fold or curl under as the diaper is maneuvered into position by the caregiver.

In this regard, and as an alternative or in combination with any of the features described herein, it may be desired that the material of which the fastening member is formed have a minimum stiffness, again, to impart to the fastening member a certain degree of resistance to bending, folding or curling. It may be desired that the fastening member have a stiffness of at least 0.0600 N/mm, more preferably at least 0.0800 N/mm, still more preferably at least 0.1000 N/mm, and even more preferably at least 0.1200 N/mm, as measured by the Stiffness Measurement Method set forth herein.

Methods for increasing stiffness of a web material that may be used to form the fastening member as described above, in addition to making the fastening member of non-elastic material, are well known, and include but are not limited to increasing the basis weight(s) of the layer component(s) laminating two or more layers to form the web material, adding stiffening films or other stiffening layers, increasing the application basis weight of adhesive used to laminate layer components, increasing the bond area for nonwoven(s) used as layer components, etc.

One or a combination of the size, weight and stiffness features described herein can help a fastening member 110 resist bending or folding at locations laterally outboard of the outer leg elastic line, while tending to promote bending or folding (hinging) of the portions of the chassis along longitudinally-oriented hinge zones 38 adjacent the fastening members. This configuration promotes easy opening of the fastening members toward the open position reflected in FIG. 2, and helps them remain that way, i.e., resist a tendency to return to a folded or bunched configuration after the diaper has been opened and laid upon a horizontal surface.

Figure 6:
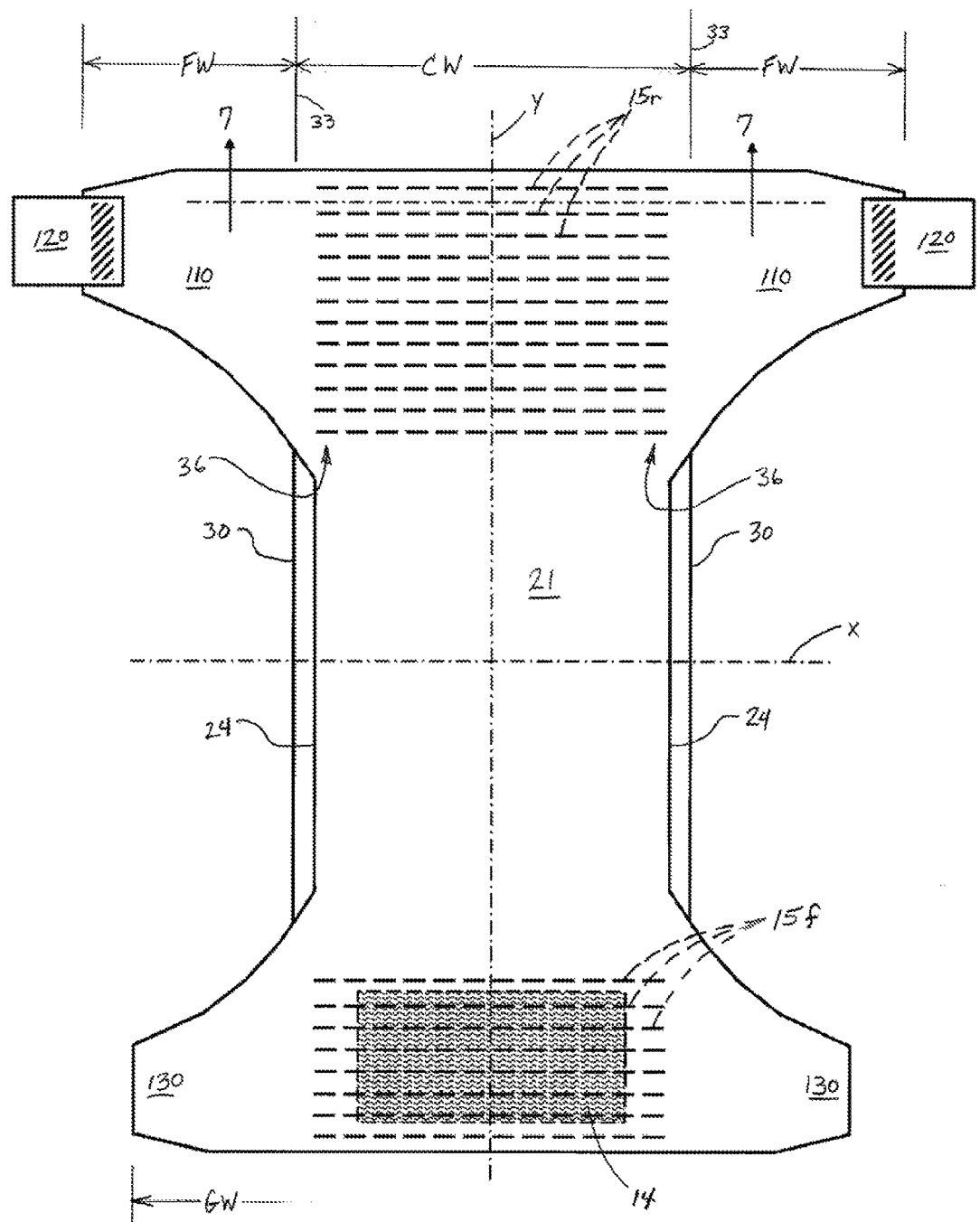
FIG. 6 is a schematic plan view of another example of a tape diaper laid out flat and in an extended condition, with garment-facing surfaces facing the viewer.
Figure 7A:
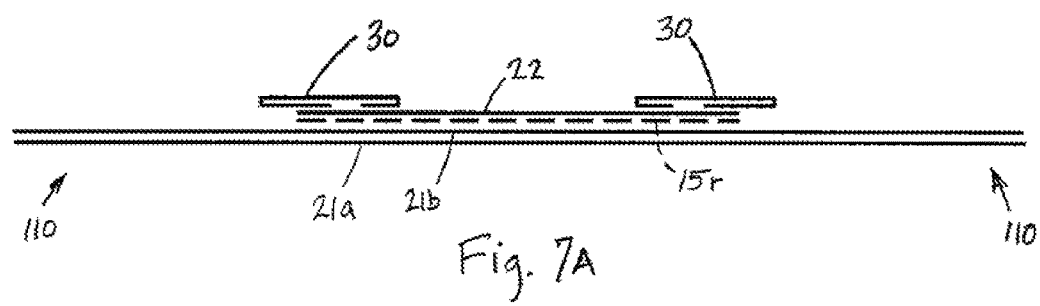
FIG. 7A is a schematic lateral cross-section of the diaper of FIG. 6 in one possible configuration, taken along line 7-7 shown in FIG. 6.
Figure 7B:
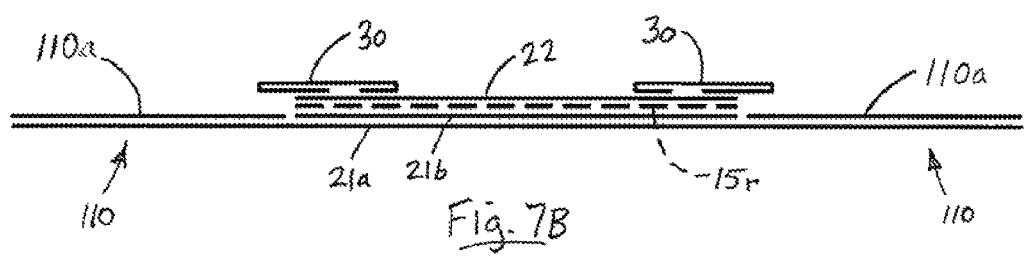
FIG. 7B is a schematic lateral cross-section of the diaper of FIG. 6 in another possible configuration, taken along line 7-7 shown in FIG. 6.
Figure 8:
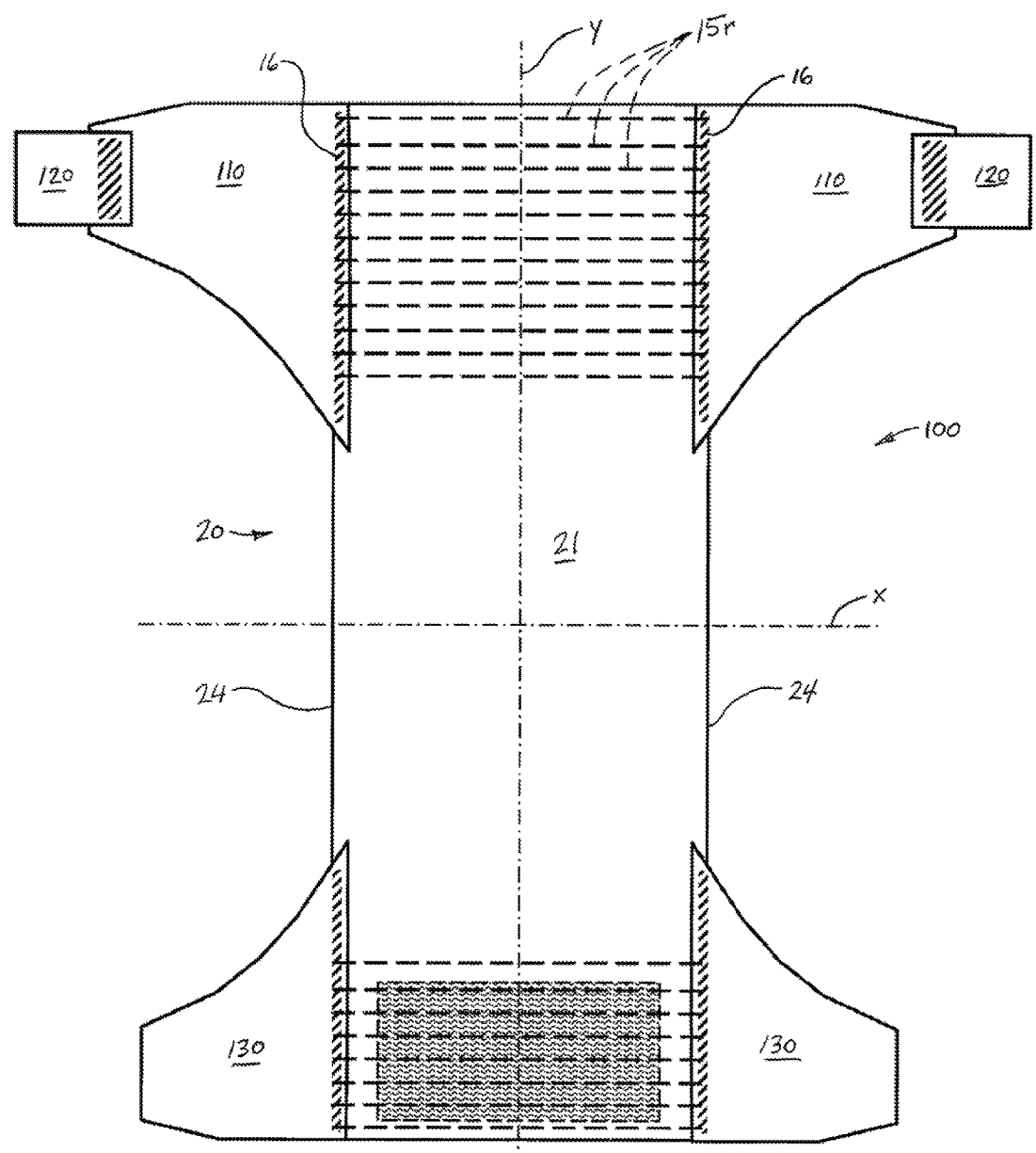
FIG. 8 is a schematic plan view of another example of a tape diaper laid out flat and in an extended condition, with garment-facing surfaces facing the viewer.
Figure 9:
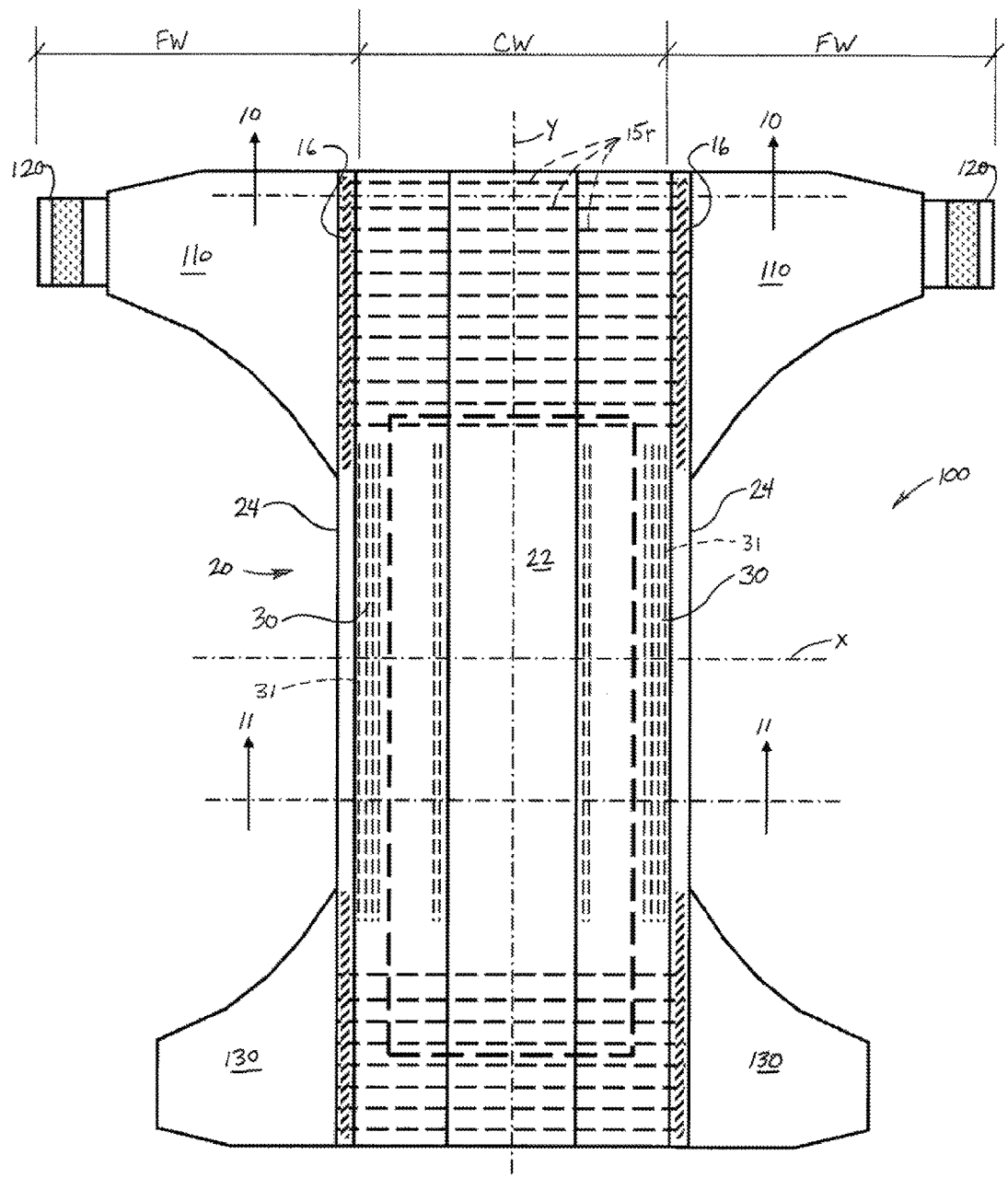
FIG. 9 is a schematic plan view of the diaper of FIG. 8, laid out flat and in an extended condition, with wearer-facing surfaces facing the viewer.
Figure 10:
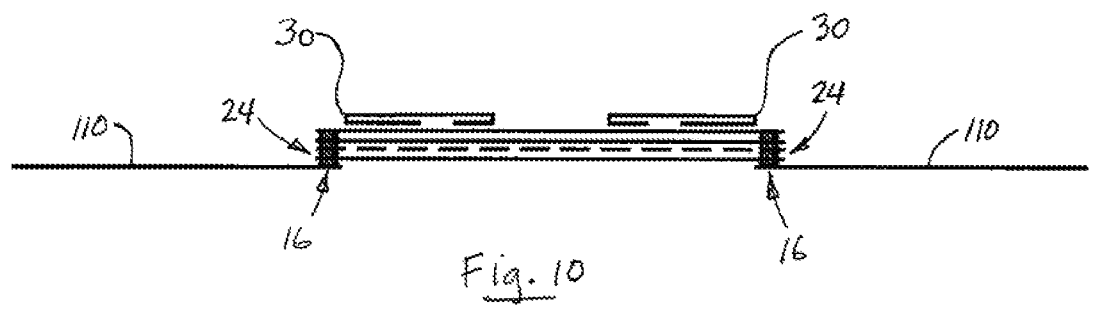
FIG. 10 is a schematic lateral cross-section of the diaper of FIG. 9 in one possible configuration, taken along line 10-10 shown in FIG. 9.
Figure 11:
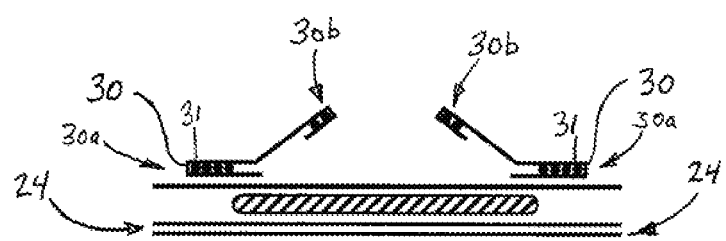
FIG. 11 is a schematic lateral cross-section of the diaper of FIG. 9 in one possible configuration, taken along line 11-11 shown in FIG. 9.
Figure 12:
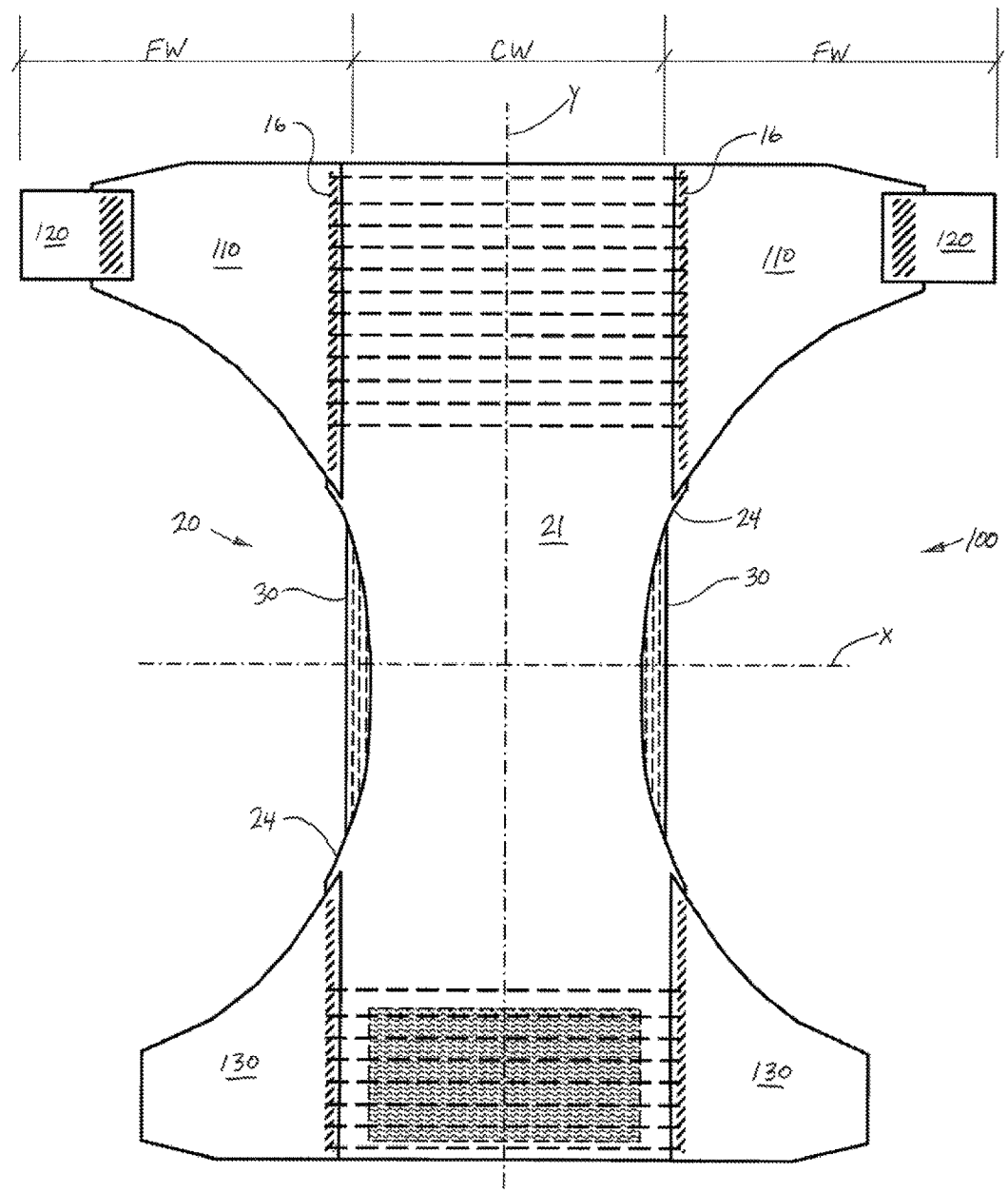
FIG. 12 is a schematic plan view of another example of a tape diaper laid out flat and in an extended condition, with garment-facing surfaces facing the viewer.

As suggested in FIGS. 6, 7A and 7B, the fastening members 110 may have at least one layer of material in common, such as the material forming outer cover 21a. This may contribute to imparting a neat, clean and uniform appearance to the features of the rear waist region. In one example illustrated in FIG. 7A, the backsheet and fastening members may have all layers in common, such as both of layers 21a and 21b. In another example illustrated in FIG. 7B, the fastening members 110 and backsheet 12 may have outer cover layer 21a in common, but have one or more other layers 110a that distinct from other components of the chassis. Layer 110a may be, for example, a second layer of nonwoven web material.

In other alternatives, as suggested in FIGS. 1, 2, 3A, 3B and 9, 10 and 12, each fastening member 110 may be separately formed and bonded to components of the chassis 20 by a mechanical bond 16. The mechanical bond may be continuous along a line segment. The mechanical bond 16 may include one or more bonded areas at which the bonded materials adhered together and/or are physically intermixed, intermingled or intertwined. In one example, the mechanical bond 16 is created by a combination of heat and compression of the bonded layers, which causes deformation and at least partial fusing of the materials at the bond site. In another example, an added adhesive is disposed between layers of the materials being bonded. As a result of the bonding and/or fusing of the bonded materials, the materials at the bond sites will have added stiffness, greater than the combined stiffness of the individual bonded materials, creating a zone of added stiffness along and within the outer perimeter of the bond 16. When combined with fastening member stiffness relative the components of the chassis as described herein, this further promotes the tendency of the chassis materials to hinge along longitudinal lines or hinge zones 38 (see FIG. 1) laterally inboard of the bond. For best chances of promoting this hinging action, it may be desirable that the bond, or a combination of two or more continuous bonds, extend along longitudinal line segment(s) for at least 75 percent of the length of the fastening member where it meets the outer leg elastic line.

It may be desired that the mechanical bond 16 be disposed either entirely laterally inboard of or entirely laterally outboard of the outer leg elastic line (rather than overlying or underlying the outer leg elastic line). This may reduce the possibility that the added layers making up the cuff structure 30 will interrupt hinging adjacent and laterally inboard of the mechanical bond.

In accordance with the description above, in one particular example, the fastening member may be formed of a laminate of three layers of spunbond polypropylene fiber nonwoven, adhered together with adhesive, having a combined basis weight of 80 gsm. In such example, the fastening member may have a surface area of 10,671 $mm^2$, a length of 145 mm and a width FW of 90 mm, as compared with a chassis width CW of 192 mm and a chassis surface area of 88,704 $mm^2$. The fastening member of this example is non-elastic.

Grasping Members

Generally, if grasping members 130 are included, they may have any of the features described herein for fastening members (including size, weight and stiffness), except that they are preferably non-elastic and lack fastening tabs. Also, preferably, they are smaller than the fastening members in one or more of width GW, length and/or surface area. This is to strike a balance between providing lay-open functionality, while avoiding overuse of materials that do not serve a useful purpose after the diaper has been applied to a wearer.

Thus, alone or in combination with any of the features described for fastening members described herein, it may be desired that each grasping member have a minimum basis weight of at least 70 gsm, and more preferably at least 80 gsm.

Alternatively or in combination with any of the features described herein, it may be desired that each grasping member have a minimum grasping member width GW of at least 37 percent, more preferably at least 39 percent, and still more preferably at least 41 percent of the chassis width CW. Herein, grasping member width GW of a grasping member is measured as the lateral distance between the outer leg elastic line adjacent the grasping member, and the distal end of the grasping member with the grasping member in a relaxed state. Chassis width CW is measured with the chassis in extended condition, and is the distance between the two outer leg elastic lines; see FIGS. 1 and 2.

In the alternative or in combination with a minimum width and/or any other features described herein, it may be desired that each grasping member have a minimum surface area (on one side) within its perimeter of at least 6 percent, more preferably at least 7 percent, and still more preferably at least 8 percent of the chassis surface area. Herein, the perimeter of the grasping member defining its surface area is the outline of the portion of the grasping member laterally outboard of the adjacent outer leg elastic line in a relaxed, flat condition.

Waist Region Elasticization

In any embodiment, it may be desirable to elasticize the waist regions of the chassis, for purposes of enhancing fit and exudate containment functionality. Particularly in the rear waist region, elasticization via inclusion of pre-strained elastic members can serve to reduce or prevent gaping of the rear waist edge away from the wearer's body when the wearer bends at the hips. This may be desired further when the fastening members are non-elastic as described herein, in which case elasticizing one or both of the waist regions of the chassis 20 may impart the elastic stretch desired about the wearer's waist in the tape diaper structure, for comfort fit and appearance. Accordingly, the chassis may include, in one example, elastic members 15f and/or 15r in the front and rear waist regions, respectively. Elastic members 15f and/or 15r may be longitudinally spaced, laterally extending strips or strands of elastomeric material disposed between the topsheet and backsheet, or between layers 21a and 21b of the backsheet. Elastic members 15f and/or 15r may be incorporated into the structure while in a pre-strained condition, upon completion of manufacturing and relaxation of the chassis structure, the elastic members will contract toward their unstrained lateral dimensions, drawing the associated chassis layers laterally to form gathers 19 (see FIG. 3B) that permit subsequent lateral elastic stretch and contraction of the waist region(s), and enhancing comfort and fit. Additionally, it is believed that having gathers in the chassis portion of the structure promotes the longitudinal hinging behavior of the chassis materials as described above, where such gathers are present.

Adding Hinging Structure in Fastening Member

Figure 13A:
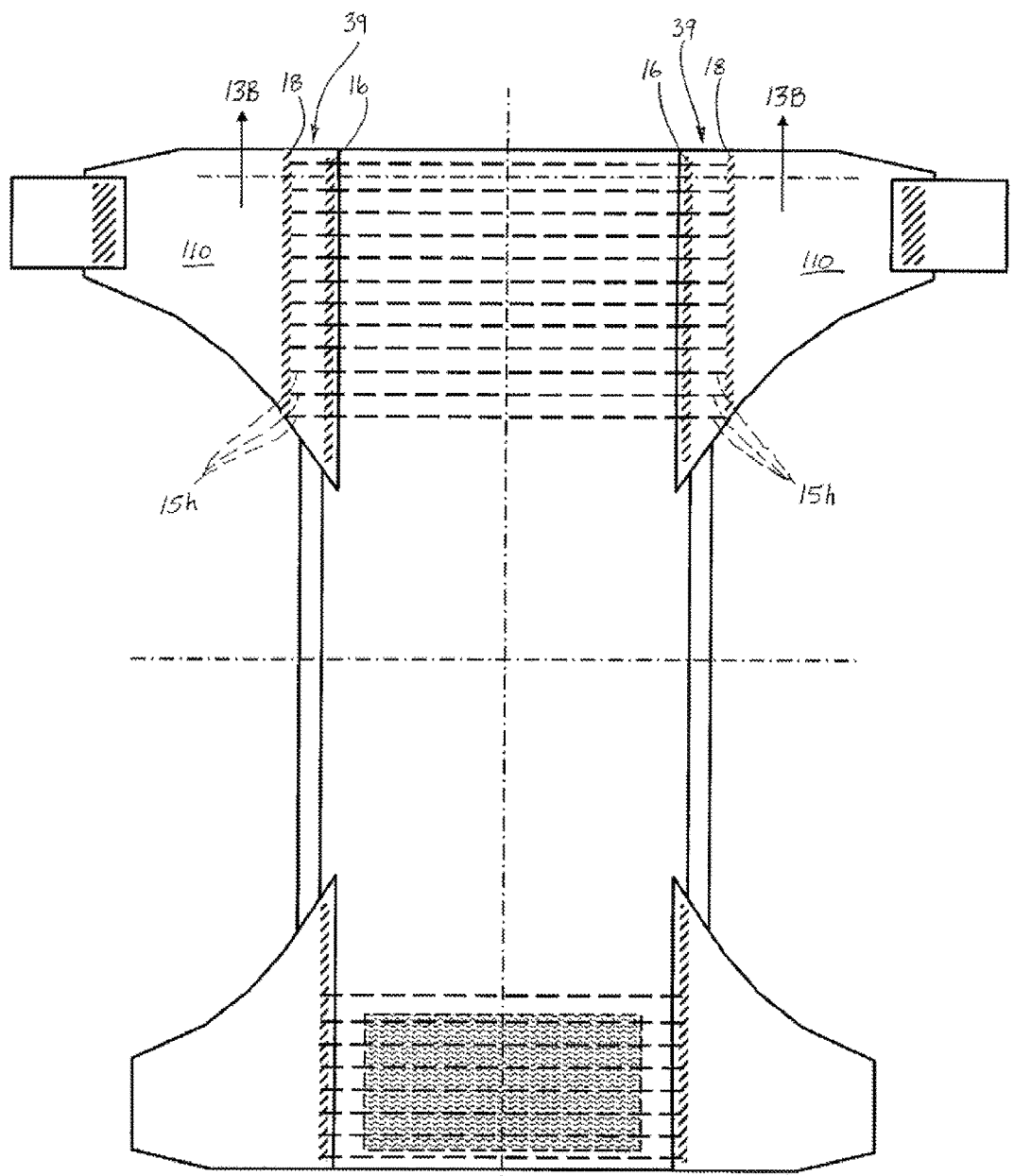
FIG. 13A is a schematic plan view of an example of a tape diaper laid out flat and in an extended condition, open and extended to the full dimensions of its web components with elastic-induced contraction pulled out, with garment-facing surfaces facing the viewer.
Figure 13B:
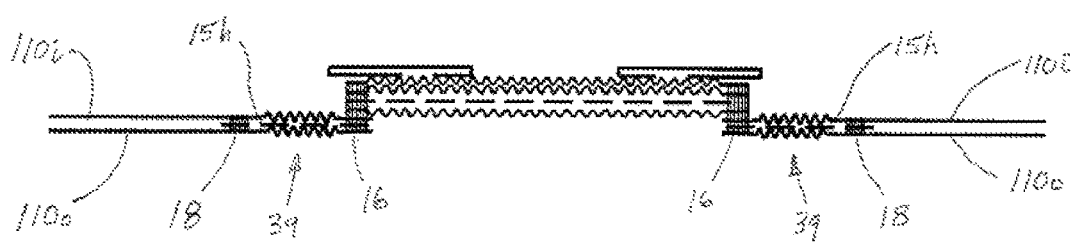
FIG. 13B is a schematic lateral partial cross-section of the diaper of FIG. 13A, take along line 13B-13B shown in FIG. 13A, and shown with the diaper in a laterally relaxed condition in which gathers form in some of the components.

As an alternative or in combination with any of the other features described herein, fastening members 110 may be imparted with added hinging structures. Referring to FIGS. 13A and 13B, fastening members 100 may include at least inner and outer layers 110i, 110o, which sandwich a plurality of hinge elastic members 15h. Inner and outer layers 110i, 110o each may be formed of nonwoven web material, polymer film material, or a combination or laminate thereof. Hinge elastic members 15h may be incorporated into the fastening members 100 in a pre-strained condition as described above for waist elastic members, and affixed at their ends at bonds 16 and 18. Upon elastic contraction, hinge elastic members 15h cause layers 100i, 110o to draw in laterally and form longitudinally-oriented gathers as shown in FIG. 13A. The relatively pliable elastic members and the gathers create a relatively flexible outer hinge zone 39 along which fastening member 110 may bend easily about bond 16, relative the remaining ungathered portion of the fastening member—in a manner similar to that the hinge zone 38 described above. Depending upon the construction of the diaper, outer hinge zone 39 may be disposed laterally inboard or laterally outboard of the outer leg elastic line.

Bonds 16 and 18 may be thermal bonds and/or adhesive bonds joining layers of the diaper and fastening member as suggested in FIG. 13A.

Consistent with the description above, the following non-limiting examples are contemplated herein:

1. A disposable diaper, comprising:
    a chassis having a front waist region, a crotch region and a rear waist region, and comprising a liquid permeable topsheet, a liquid impermeable backsheet, and an absorbent core structure disposed between the topsheet and the backsheet, the chassis having a chassis width and the chassis having a chassis surface area and
    left and right, laterally extending fastening members extending from the rear region, the fastening members each having a basis weight of at least 90 gsm, more preferably at least 100 gsm, still more preferably at least 110 gsm, and still more preferably at least 120 gsm, each fastening member having a fastening member width of at least 60 percent, more preferably at least 65 percent, still more preferably at least 70 percent, and even more preferably at least 75 percent, of the chassis width, and a fastening member surface area of at least 10 percent, more preferably at least 11 percent, and still more preferably at least 12 percent, of the chassis surface area.
2. The diaper of example 1 wherein each fastening member has a stiffness of at least 0.0600 N/mm, more preferably at least 0.0800 N/mm, still more preferably at least 0.1000 N/mm, and even more preferably at least 0.1200 N/mm.
3. The diaper of either of examples 1 or 2 comprising laterally-oriented, pre-strained elastic members in one or both the front waist region and the rear waist region.
4. The diaper of any of the preceding examples wherein the fastening members are non-elastic.
5. The diaper of any of the preceding examples wherein the absorbent core structure comprises no more than 10 percent by weight cellulosic fibers.
6. The diaper of any of the preceding examples further comprising left and right, laterally extending grasping members extending from the front waist region, the grasping members each having a basis weight of at least 70 gsm, more preferably at last 80 gsm, the web material of each grasping member having a grasping member width of at least 37 percent, more preferably at least 39 percent, and still more preferably at least 41 percent, of the chassis width extending laterally beyond the backsheet, and a grasping member surface area of at least 6 percent, more preferably at least 7 percent, and still more preferably at least 8 percent, of the chassis surface area.
7. The diaper of any of the preceding examples wherein the backsheet and the fastening members have at least one layer of material in common.
8. The diaper of example 6 wherein the backsheet and the grasping members have at least one layer of material in common.
9. The diaper of any of the preceding examples wherein the fastening members each comprise a laminate of at least two layers of material.
10. The diaper of example 6 wherein the grasping members each comprise a laminate of at least two layers of material.
11. A disposable diaper, comprising:
    a chassis having a front waist region, a crotch region and a rear waist region, and comprising a liquid permeable topsheet, a liquid impermeable backsheet, and an absorbent core structure disposed between the topsheet and the backsheet, the chassis having a chassis width and the chassis having a chassis surface area and left and right, laterally extending fastening members extending from the rear waist region, the fastening members each having a first basis weight of at least 90 gsm, more preferably at least 100 gsm, still more preferably at least 110 gsm, and still more preferably at least 120 gsm, each fastening member having a fastening member width of at least 60 percent, more preferably at least 65 percent, still more preferably at least 70 percent, and even more preferably at least 75 percent, of the chassis width, and a fastening member surface area of at least 10 percent, more preferably at least 11 percent, and still more preferably at least 12 percent, of the chassis surface area;

each fastening member being formed separately of the chassis and being attached to one or more web components of the chassis by one or more longitudinally-oriented mechanical bonds, and in combination extending along one or more longitudinal line segments for at least 75 percent of the length of the fastening member.

12. The diaper of example 11 wherein each of the mechanical bonds is continuous.
13. The diaper of any of examples 11-12 wherein the combination of the topsheet and the backsheet has a second basis weight when the chassis is in an extended condition, and the first basis weight is greater than the second basis weight by at least 280 percent, more preferably at least 360 percent, even more preferably at least 440 percent, and still more preferably at least 520 percent.
14. The diaper of any of examples 11-13 comprising one or more pre-strained, laterally-extending elastic members disposed in or on the chassis between the fastening members, operable to impart gathers in either or both the topsheet and the backsheet.
15. The diaper of any of examples 11-14 wherein the backsheet comprises a laminate of a liquid impermeable film and a nonwoven outer cover layer.
16. The diaper of example 15 comprising one or more pre-strained, laterally-extending elastic members disposed between the fastening members and between the topsheet and the nonwoven outer cover layer, operable to impart gathers in either or both the topsheet and the backsheet.
17. The diaper of any of examples 11-16 further comprising a pair of longitudinal cuff structures affixed to the chassis on a wearer-facing side thereof.
18. The diaper of example 17 wherein the mechanical bond is disposed laterally outboard of the outer leg elastic line.
19. The diaper of example 17 wherein the mechanical bond is disposed laterally inboard of the outer leg elastic line.
20. The diaper of any of examples 11-19 wherein each fastening member has a stiffness of at least 0.0600 N/mm, more preferably at least 0.0800 N/mm, still more preferably at least 0.1000 N/mm, and even more preferably at least 0.1200 N/mm.
21. The diaper of any of examples 11-20 wherein the fastening members are non-elastic.
22. The diaper of any of examples 11-21 wherein the absorbent core structure comprises no more than 10 percent by weight cellulosic fibers.
23. The diaper of any of examples 11-22 further comprising left and right, laterally extending grasping members extending from the front region, the grasping members each comprising a web material having a basis weight of at least 70 gsm, and more preferably at least 80 gsm, the web material of each grasping member having a grasping member width of at least 37 percent of the chassis width, and a grasping member surface area of at least 6 percent, more preferably at least 7 percent, and still more preferably at least 8 percent, of the chassis surface area.
24. The diaper of any of examples 11-23 wherein the fastening members each comprise a laminate of at least two layers of material.

Stiffness Measurement Method

Bending stiffness of the fastening member (back) and grasping member (front) (hereinafter in this Stiffness Measurement Method description, back and front "ears") is measured on a constant rate of extension tensile tester (a suitable instrument is the MTS Alliance using Testworks 4.0 Software, as available from MTS Systems Corp., Eden Prairie, Minn.) using a load cell for which the forces measured are within 10% to 90% of the limit of the cell.

The bottom stationary fixture consists of 2 flat horizontal rectangular plates made of polished stainless steel, 120 mm long (horizontal dimension front to back) by 38 mm wide (horizontal dimension side-to-side) by 10 mm thick (vertical dimension). The largest planar surfaces of these plates are oriented perpendicular to the motion of the crossbeam of the tensile tester. The plates are arranged in aligned side-by-side orientation with their largest planar surfaces in the same plane, their lengths parallel each other, their widths aligned, and with a gap between them (such that the gap is uniform and extends for 120 mm). Furthermore, the two plates are configured so that they can be moved away from each other so that the gap can be set between them while maintaining the same orientation. The edges of the plates along the gap are square with minimal curvature.

The top movable fixture consists of a polished stainless steel blade 120 mm long (horizontal dimension front to back) by 3.28 mm thick (horizontal dimension side-to-side) 45 mm high (vertical dimension). The bottom edge of the blade that contacts the specimen has a radius of curvature of 1.64 mm.

Both fixtures have mounts that fit the respective position in the tensile tester frame and lock into position such the top blade vertical dimension is orthogonal to the horizontal largest planar surfaces of the plates, with the blade thickness perpendicular to and centered over the gap between the plates. The plates are adjusted to a gap of 5 mm with the blade thickness centered over the gap. The gage length (measured vertically from the bottom edge of the blade to the plane occupied by the top surfaces of the plates) is set to 15 mm.

All testing is performed in a room controlled at 23° C.±3° C. and 50%±2% relative humidity. Samples are conditioned at 23° C.±3° C. and 50%±2% relative humidity for two hours prior to testing.

A specimen 20 mm in the longitudinal direction of the article and 15 mm in the lateral direction of the article is cut from each back ear, and if present, each front ear of the article. To identify the outline of the specimen to be cut, locate the longitudinal centerline between the laterally outboard-most line along which the ear is attached to the chassis and the laterally outboard-most end of the ear (where the ear includes a fastening tab, the laterally outboard-most end of the fastening tab). Center the outline of the specimen longitudinally and laterally along this centerline, and cut the specimen from the ear along the outline.

Program the tensile tester for a compression test, to move the crosshead down at a rate of 50 mm/min for 35 mm collecting force (N) and displacement (m) data at 400 Hz, and return the crosshead to the original gage. Place the specimen under the blade, bridging the gap with the 20 mm side parallel to the blade length dimension and the edges of the gap, and with the specimen centered over the gap. Zero the crosshead and load cell. Start the run and collect data.

Construct a graph of force (N) verses displacement (m). Calculate the maximum slope of the curve using a line segment that has a length of at least 25% of the maximum force. Calculate the bending stiffness in N/m to the nearest 0.1 N/m. Measurements are repeated in like fashion for specimens from 5 back ears from the left sides of 5 diaper samples and the matching 5 back ears from the right sides of the diaper samples and report the average all ten values to the nearest 0.1 N/m. If present, repeat measurements on the front ears as done for the back ears, and report the average to the nearest 0.1 N/m.

Hysteresis Test

Obtain samples of subject material sufficient to provide for a gauge length of at least 15 mm along the direction of stretch in the Test, and should be of a constant width (perpendicular to the direction of stretch in the Test) of at least 5 mm.

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate grips and load cell. The grips must have flat surfaces and must be wide enough to grasp the sample along its full width. Also, the grips should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) at 15 mm.

4. Place the sample in the flat surfaces of the grips such that the uniform width lies along a direction perpendicular to the gauge length direction. Secure the sample in the upper grips, let the sample hang slack, then close the lower grips. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length×100.

5(a) First cycle loading: Pull the sample to the specified strain (herein, 100%) at a constant cross head speed of 100 mm/min. Report the stretched sample length between the grips as $l_{max}$.

5(b) First cycle unloading: Hold the sample at the specified strain for 30 seconds and then return the crosshead to its starting position (0% strain or initial sample length, $l_{ini}$) at a constant cross head speed of 100 mm/min. Hold the sample in the unstrained state for 1 minute.

5(c) Second cycle loading: Pull the sample to the specified strain at a constant cross head speed of 100 mm/min.

5(d) Second cycle unload: Next, return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

i. Length of sample between the grips at a slack preload of 0.02 N/cm ($l_{ini}$) to the nearest 0.001 mm.

ii. Length of sample between the grips on first cycle at the specified strain ($l_{max}$) to the nearest 0.001 mm.

iii. Length of sample between the grips at a second cycle load force of 0.02 N/cm ($l_{ext}$) to the nearest 0.001 mm.

iv. % set, which is defined as $(l_{ext}-l_{ini})/(l_{max}-l_{ini})*100\%$ to the nearest 0.01%. The testing is repeated for six separate samples and the average and standard deviation reported.

The Hysteresis Test can be suitably modified depending on the expected attributes and/or properties of the particular material sample to be measured. For example, the Test can be suitably modified where a sample of the length and width specified above are not available from the subject pant.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A disposable diaper, comprising:
   a chassis having a front waist region, a crotch region and a rear waist region, and comprising a liquid permeable topsheet, a liquid impermeable backsheet, and an absorbent core structure disposed between the topsheet and the backsheet, the chassis having a chassis width and the chassis having a chassis surface area; and
   left and right, laterally extending fastening members extending from the rear waist region, the fastening members each having a basis weight of at least 90 gsm, each fastening member having a fastening member width of at least 60 percent of the chassis width and a fastening member surface area of at least 10 percent of the chassis surface area; and left and right, laterally extending discrete grasping members extending from the front waist region, the grasping members each having a basis weight of at least 70 gsm, each grasping member having a grasping member width of at least 37 percent of the chassis width, and each grasping member having a grasping member surface area of at least 6 percent of the chassis surface area;

wherein the grasping members are non-elastic; and wherein the grasping members are smaller than the fastening members in one or more of width, length, or surface area.

2. The diaper of claim 1 wherein each fastening member has a stiffness of at least 0.0600 N/mm.

3. The diaper of claim 1 comprising laterally-oriented, pre-strained elastic members in one or both of the front waist region and the rear waist region.

4. The diaper of claim 1 wherein the fastening members are non-elastic.

5. The diaper of claim 1 wherein the absorbent core structure comprises no more than 10 percent by weight cellulosic fibers.

6. The diaper of claim 1 wherein the fastening members each comprise a laminate of at least two layers of material.

7. The diaper of claim 1 wherein the grasping members are free of fastening tabs.

8. The diaper of claim 1 wherein the fastening members comprise hinge elastic members in a pre-strained condition.

9. A disposable diaper, comprising:
a chassis having a front waist region, a crotch region and a rear waist region, and comprising a liquid permeable topsheet, a liquid impermeable backsheet comprising a laminate of a liquid impermeable film and a nonwoven outer cover layer, and an absorbent core structure disposed between the topsheet and the backsheet, the chassis having a chassis width and the chassis having a chassis surface area; and left and right, laterally extending fastening members extending from the rear waist region, the fastening members each having a first basis weight of at least 90 gsm, each fastening member having a fastening member width of at least 60 percent of the chassis width, and a fastening member surface area of at least 10 percent of the chassis surface area, each fastening member being attached to one or more web components of the chassis by one or more longitudinally-oriented mechanical bonds extending along one or more longitudinal line segments for at least 75 percent of the length of the fastening member; and left and right, laterally extending discrete grasping members extending from the front waist region, the grasping members each having a basis weight of at least 70 gsm, each grasping member having a grasping member width of at least 37 percent of the chassis width, and each grasping member having a grasping member surface area of at least 6 percent of the chassis surface area;

wherein the grasping members are non-elastic; and wherein the grasping members are smaller than the fastening members in surface area.

10. The diaper of claim 9 wherein each of the mechanical bonds is continuous.

11. The diaper of claim 9 wherein the topsheet and the backsheet have a combined second basis weight, and wherein the first basis weight is greater than the second basis weight by at least 280 percent.

12. The diaper of claim 9 comprising one or more pre-strained, laterally-extending elastic members disposed in or on the chassis between the fastening members, operable to impart gathers in either or both the topsheet and the backsheet.

13. The diaper of claim 9 comprising a pair of longitudinal cuff structures affixed to the chassis on a wearer-facing side thereof.

14. The diaper of claim 13 wherein the one or more mechanical bonds are disposed laterally outboard of an outer leg elastic line.

15. The diaper of claim 13 wherein the one or more mechanical bonds are disposed laterally inboard of an outer leg elastic line.

16. The diaper claim 9 wherein each fastening member has a stiffness of at least 0.0600 N/mm.

17. The diaper of claim 9 wherein the fastening members are non-elastic.

18. The diaper of claim 9 wherein the absorbent core structure comprises no more than 10 percent by weight cellulosic fibers.

19. The diaper of claim 9 wherein the fastening members each comprise a laminate of at least two layers of material.

20. The diaper of claim 9 wherein the grasping members are free of fastening tabs.

* * * * *